(12) United States Patent  (10) Patent No.: US 6,902,398 B1
Segal  (45) Date of Patent: Jun. 7, 2005

(54) BITE TRAY WITH REMOVABLE INSERT

(75) Inventor: Alan J. Segal, Hale (GB)

(73) Assignee: Astek Innovations Limited, Cheshire (GB)

( * ) Notice: Subject to any disclaimer, the term of this patent is extended or adjusted under 35 U.S.C. 154(b) by 144 days.

(21) Appl. No.: 10/148,048

(22) PCT Filed: Nov. 24, 2000

(86) PCT No.: PCT/GB00/04460

§ 371 (c)(1),
(2), (4) Date: Aug. 12, 2002

(87) PCT Pub. No.: WO01/37754

PCT Pub. Date: May 31, 2001

(30) Foreign Application Priority Data

Nov. 25, 1999  (GB) ............................................. 9927958

(51) Int. Cl.[7] ................................................ A61C 9/00
(52) U.S. Cl. .............................. 433/38; 433/37; 433/45
(58) Field of Search .............................. 433/38, 45, 46, 433/37, 41–43, 71

(56) References Cited

U.S. PATENT DOCUMENTS

| 1,584,092 | A |   | 5/1926  | Harris ........................... 433/38 |
| 3,045,349 | A |   | 7/1962  | Mars ............................ 433/43 |
| 3,468,029 | A |   | 9/1969  | Moore .......................... 433/38 |
| 3,501,837 | A |   | 3/1970  | Clark ........................... 433/38 |
| 3,987,548 | A |   | 10/1976 | Jones ........................... 433/45 |
| 4,204,323 | A |   | 5/1980  | Dailey et al. .................. 433/38 |
| 4,449,927 | A |   | 5/1984  | Taylor et al. ................. 433/38 |
| 5,297,960 | A |   | 3/1994  | Burns .......................... 433/41 |
| 5,752,826 | A |   | 5/1998  | Andreiko ...................... 433/41 |
| 5,820,372 | A |   | 10/1998 | Jones .......................... 433/38 |
| 6,302,690 | B1 | * | 10/2001 | Brandhorst et al. ........... 433/45 |

FOREIGN PATENT DOCUMENTS

DE  200 05 383 U  5/2000

* cited by examiner

*Primary Examiner*—John J Wilson
(74) *Attorney, Agent, or Firm*—Hollander Law Firm, P.L.C.

(57) ABSTRACT

Dental apparatus for recording the interdental relationship of posterior teeth has spaced apart longitudinal supports (1, 2) between which longitudinal side members (7, 8) of a bite tray (5) are releasably engaged. The bite tray has supporting material (6) for supporting impression material, between the side members (7, 8). The side members (7, 8) may extend over inner faces of the longitudinal supports (1, 2) to protect against contact between the impression material and the supports (1, 2). The longitudinal members (7, 8) may be channel members which slide along or snap-fit over rail-shaped supports (1, 2). In an alternative embodiment the side members may engage slots (13, 14 or 18, 19) in the supports (11, 12 or 16, 17).

10 Claims, 8 Drawing Sheets

BITE TRAY WITH REMOVABLE INSERT

This application is a 371 national stage application of international application PCT/GB00/04460 filed Nov. 24, 2000, and claiming priority from British patent application 9927958.0 filed Nov. 25, 1999.

This invention relates to dental apparatus and, more particularly, to dental apparatus for recording the interdental relationship of posterior teeth prior to the production of dental prosthetics.

In the production of dental prosthetics it has long been known to use dental impression wax supported on upper and lower sides of a disposable bite tray insert.

It is also known to provide a support device for the bite tray insert, as described in U.S. Pat. No. 4,449,927, which comprises a pair of spaced apart bite tray holders in the form of linked parallel open channels which are connected to a handle structure.

The bite tray insert used with this known device consists of a body of gauze material suspended along its longitudinal edges by attached strips of cardboard which are engaged longitudinally within the holder channels.

In operation the strips of cardboard must be carefully inserted into the channels of the known device due to the relatively frail nature of the cardboard. Thereafter the operator of the device applies dental impression material to both sides of the gauze material followed by locating the device in a patient's mouth between the upper and lower posterior teeth so that a bite impression can be recorded in the impression material.

This known device possess several significant drawbacks.

A first drawback is a consequence of the channel configuration of the known device which obscures a significant proportion of the gauze of the bite tray insert and thus makes it difficult for the dentist to correctly position the instrument prior to recording an impression.

A second drawback is that after an impression has been made in the impression material and the model casting process completed, it is difficult to remove the bite tray insert from the channels of the device for disposal without damaging the device in the process due to adhesion of the impression material to the device.

Furthermore, due to the intrinsic nature of the impression material and the contact between it and the channels of the device, it is difficult to remove the impression material from the channels of the device before autoclaving. Obviously, this is highly undesirable when such a device is frequently required in a busy dental practice.

The present invention has been made from a consideration of the drawbacks with the known device.

According to a first aspect of the present invention therefore there is provided dental apparatus for use with a bite tray insert comprising a body of supporting material with opposed edges having longitudinal members thereat, said apparatus comprising a pair of spaced apart bite tray insert supports which are adapted for releasable engagement with the longitudinal members of the bite tray insert, whereby the supporting material is suspended between inner faces of the supports characterised in that at least one, and preferably each, of the said longitudinal members is adapted to extend over at least a part of the said inner face of the respective bite tray insert support.

According to a second aspect of the present invention there is provided dental apparatus for use with a bite tray insert comprising a body of supporting material with opposed edges having longitudinal members thereat, said apparatus comprising a pair of spaced apart bite tray insert supports which are adapted for releasable engagement with the longitudinal members of the bite tray insert, whereby the supporting material is suspended between inner faces of the support and characterised in that at least one, and preferably each of the longitudinal members is configured to receive therewith at least part of one of the respective bite tray insert supports thereby to effect said releasable engagement.

With this arrangement, insofar as the longitudinal members of the bite tray insert act to keep the impression material away from the apparatus, cleaning and sterilising of the apparatus by autoclaving can be effected in a convenient and effective manner.

In addition, the performance of the device of the present invention is enhanced as the impression material is forced towards the longitudinal members of the bite tray insert. Intimate contact between the impression material and these longitudinal members aids the success of the impression produced. To help assist this contact ribbed features may be included on the inside face of the longitudinal members.

According to a third aspect of the present invention there is provided a bite tray insert comprising a body of supporting material with opposed edges having longitudinal members thereat, wherein at least one and preferably each of said longitudinal members is configured to receive therewithin at least part of a support of a dental apparatus as described above.

In a preferred embodiment both of the longitudinal members of the bite tray insert are capable of receiving at least a part of a bite tray insert support therein.

Preferably the longitudinal members of the bite tray insert are grooved members. The grooved members of the bite tray insert may have at least one open end. The body of supporting material is preferably connected along each of its two longitudinal edges to the rear sides of the grooved members such that the grooved members extend outwardly in relation to each other. Preferably the arrangement is such that the longitudinal members are engageable with the supports by sliding longitudinally thereof.

In a preferred embodiment of the invention the width of the body of supporting material of the bite tray insert is substantially the same width as the distance between the inner faces of the bite tray insert supports. Typically, the body of material of the bite tray insert is of a perforate or woven construction. The body of material of the bite tray insert can be made from a plastics gauze material or, alternatively, from a woven textile material.

The longitudinal members of the bite tray insert may be made from any suitable material, such as a plastics, rubber or card material. The bite tray insert is preferably made so as to be disposable after use. The longitudinal members suitably may be rigid or relatively stiff or self supporting especially where such members are intended to slide longitudinally onto the supports as aforesaid. However, in an alternative embodiment the longitudinal members of the bite tray insert may be made with a resilient self supporting structure to allow said members to snap-fit over the bite tray insert supports. The snap-fit connection can permit the bite tray insert to be brought into connection with the bite tray insert supports transversely as well as or instead of sliding longitudinally therealong.

At least one of the bite tray insert supports may comprise a longitudinal rail which is slidably connectable with or insertable within the respective longitudinal member of the bite tray insert. Ideally, both bite tray insert supports comprise longitudinal rails which are insertable respectively into the longitudinal members of the bite tray insert.

The bite tray insert supports are preferably interconnected at one end by means of a frame structure, the supports having a free opening therebetween at the opposite end. Preferably also the apparatus is provided with a handle which may be connected to one of the supports or the frame structure. The handle may extend outwardly from one of the bite tray supports at an acute angle away from the support at the opposite end to the frame structure.

The frame structure is preferably made from a material which is reusable and autoclavable. The frame structure may be made from any suitable rigid or resilient material such as a plastics material or metal material. Preferably the frame structure is made from a moulded plastics material. The frame structure and handle may be integral and be made as a one piece moulding.

The bite tray insert supports may be provided with an abutment means in order to limit movement of the longitudinal members of the bite tray insert along said supports. The abutment means may extend from the outer faces of the bite tray insert supports. Each of the bite tray insert supports may have two abutment means.

According to a fourth aspect of the present invention therefore there is provided dental apparatus for use with a bite tray insert comprising a body of supporting material with opposed edges having longitudinal members thereat, said apparatus comprising a pair of spaced apart bite tray insert supports which are adapted for releasable engagement with the longitudinal members of the bite tray insert, whereby the supporting material is suspended between inner faces of the support and wherein the bite tray insert supports each contain an elongate aperture therethrough, each aperture being adapted to receive transversely therethrough and retain a respective one of the longitudinal members, the longitudinal members being deflectable to permit this.

According to a fifth aspect of the present invention there is provided dental apparatus for use with a bite tray insert comprising a body of supporting material with opposed edges having longitudinal members thereat, said apparatus comprising a pair of spaced apart bite tray insert supports which are adapted for releasable engagement with the longitudinal members of the bite tray insert, whereby the supporting material is suspended between inner faces of the supports and wherein each bite tray insert support is provided with a longitudinal open ended slit therethrough to receive therealong a respective one of the longitudinal members of the bite tray insert, each such member having an upstanding retaining flange adapted to fit alongside the outer face of the respective support.

In order that the present invention can be more readily understood specific embodiments thereof will be now be described by way of example only with reference to the accompanying drawings in which.

Figure 4:
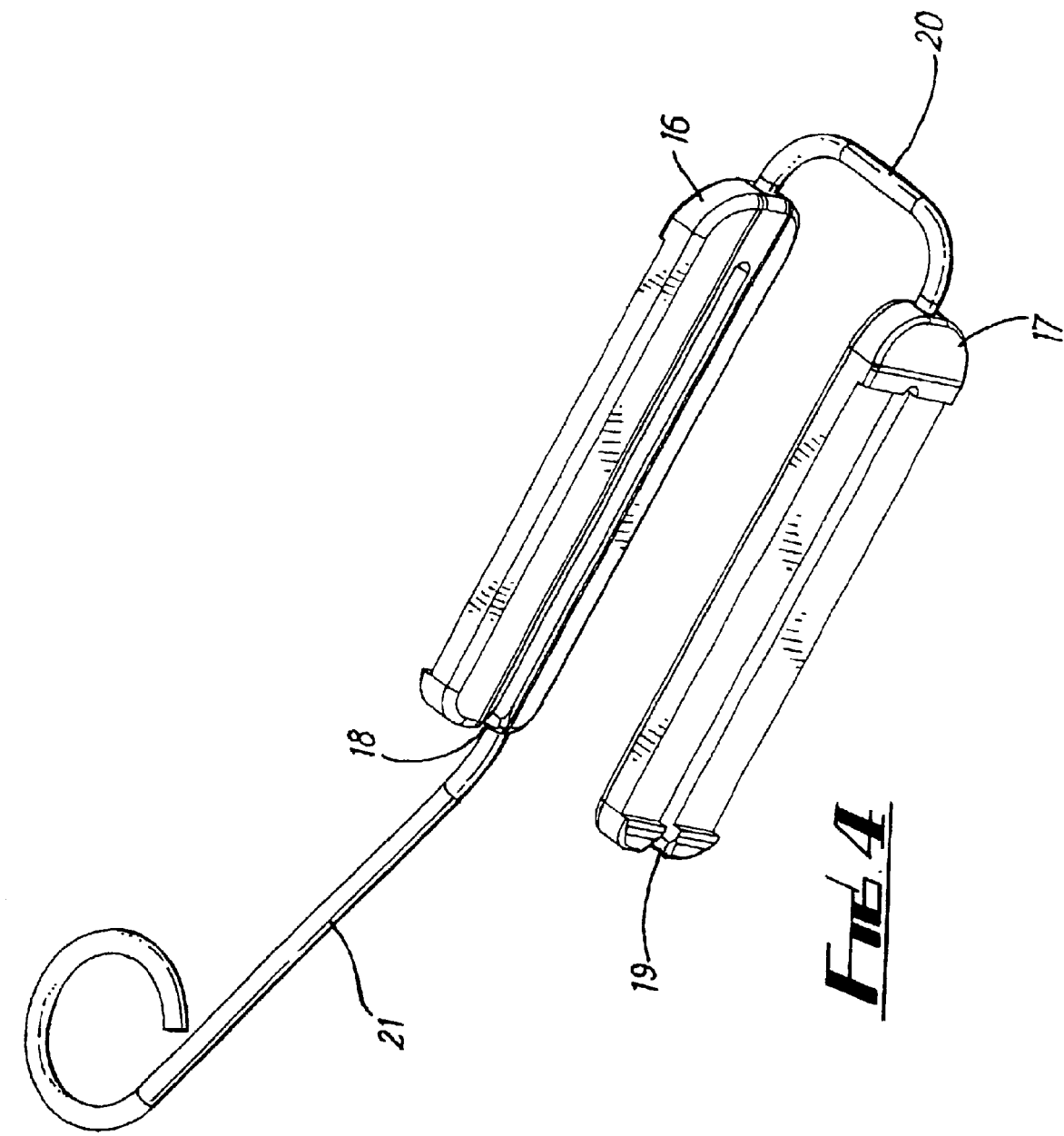
FIG. 4 is a perspective view of a third embodiment of the dental apparatus of the invention.
Figure 5:
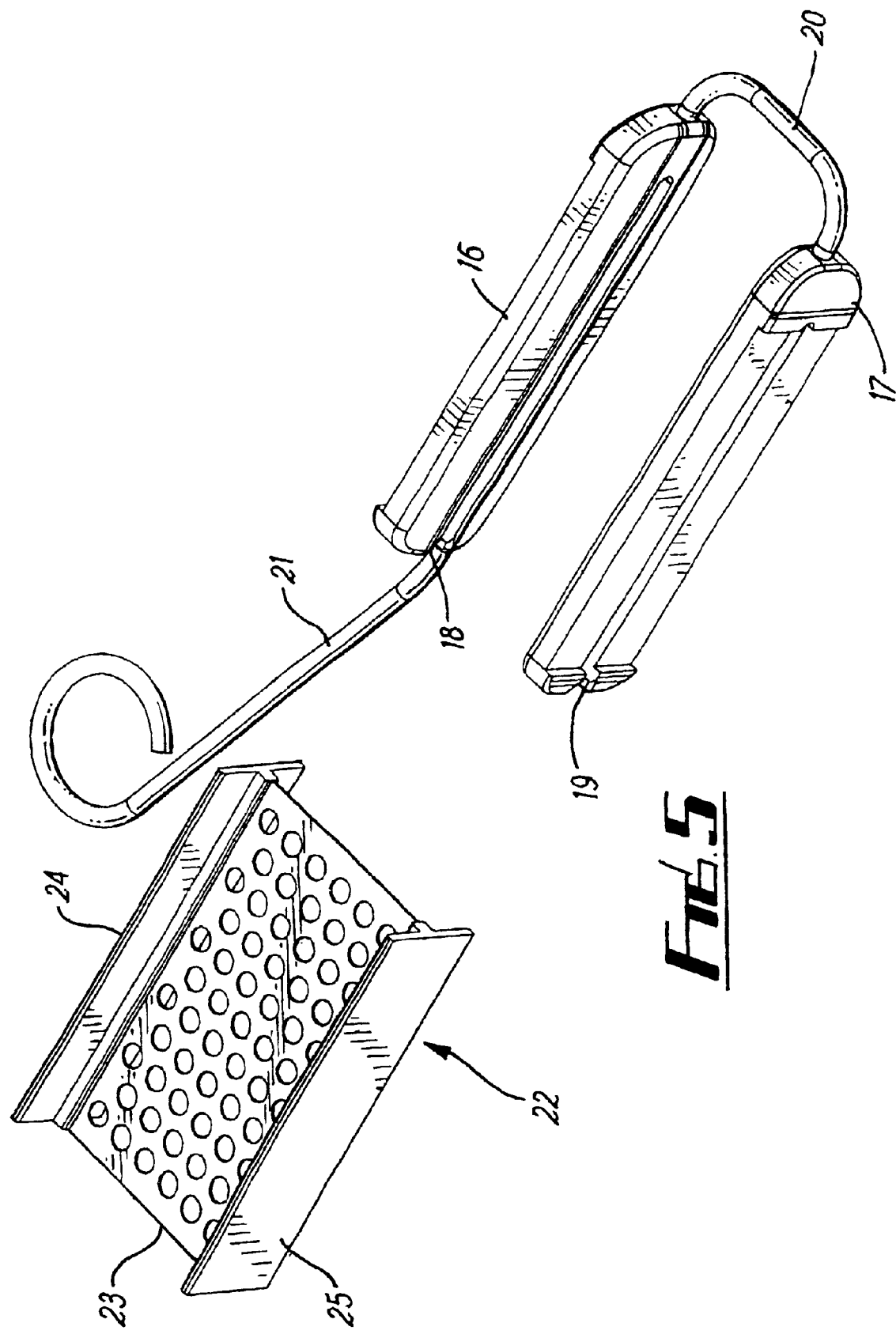
Figure 6:
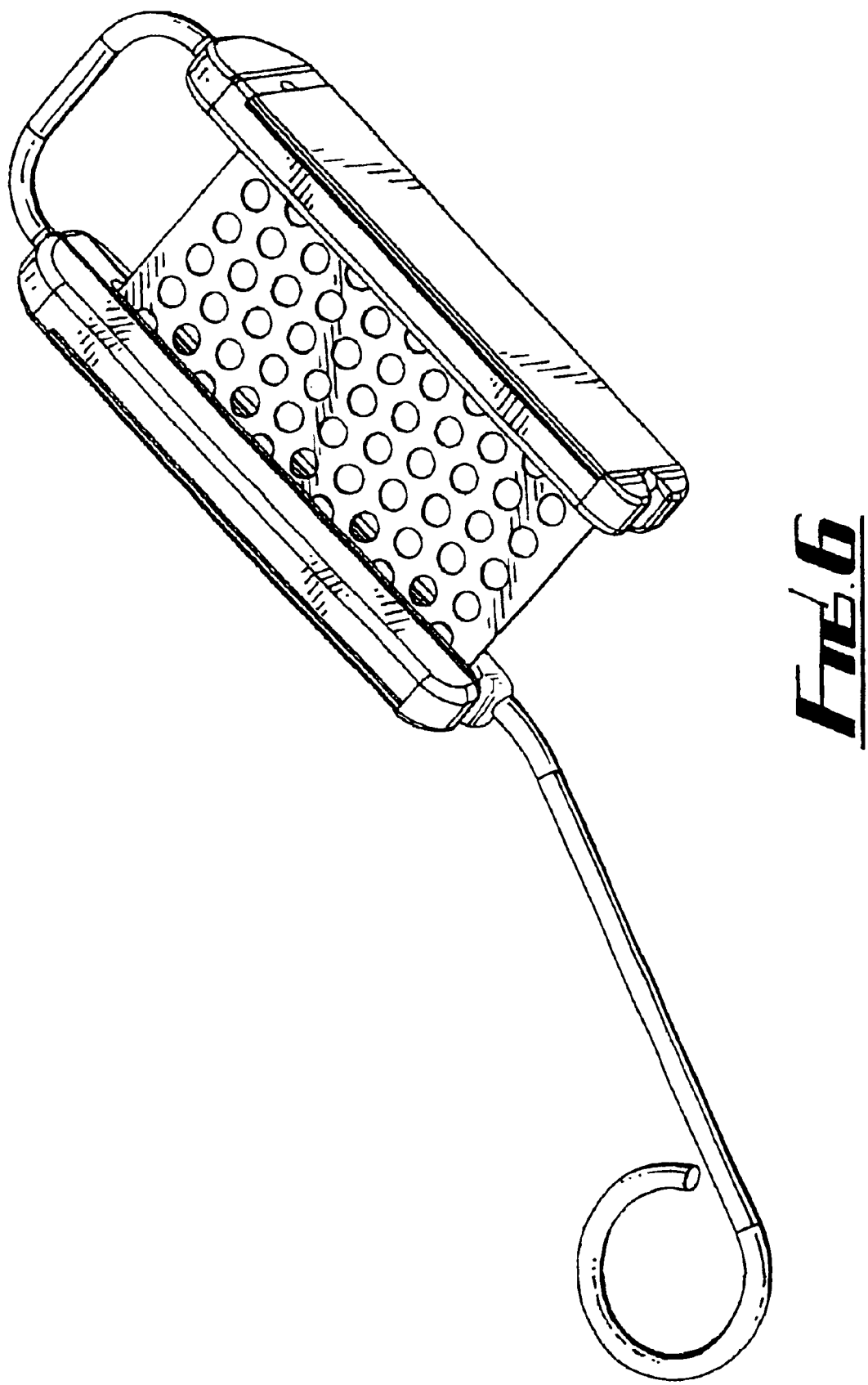
Figure 1:
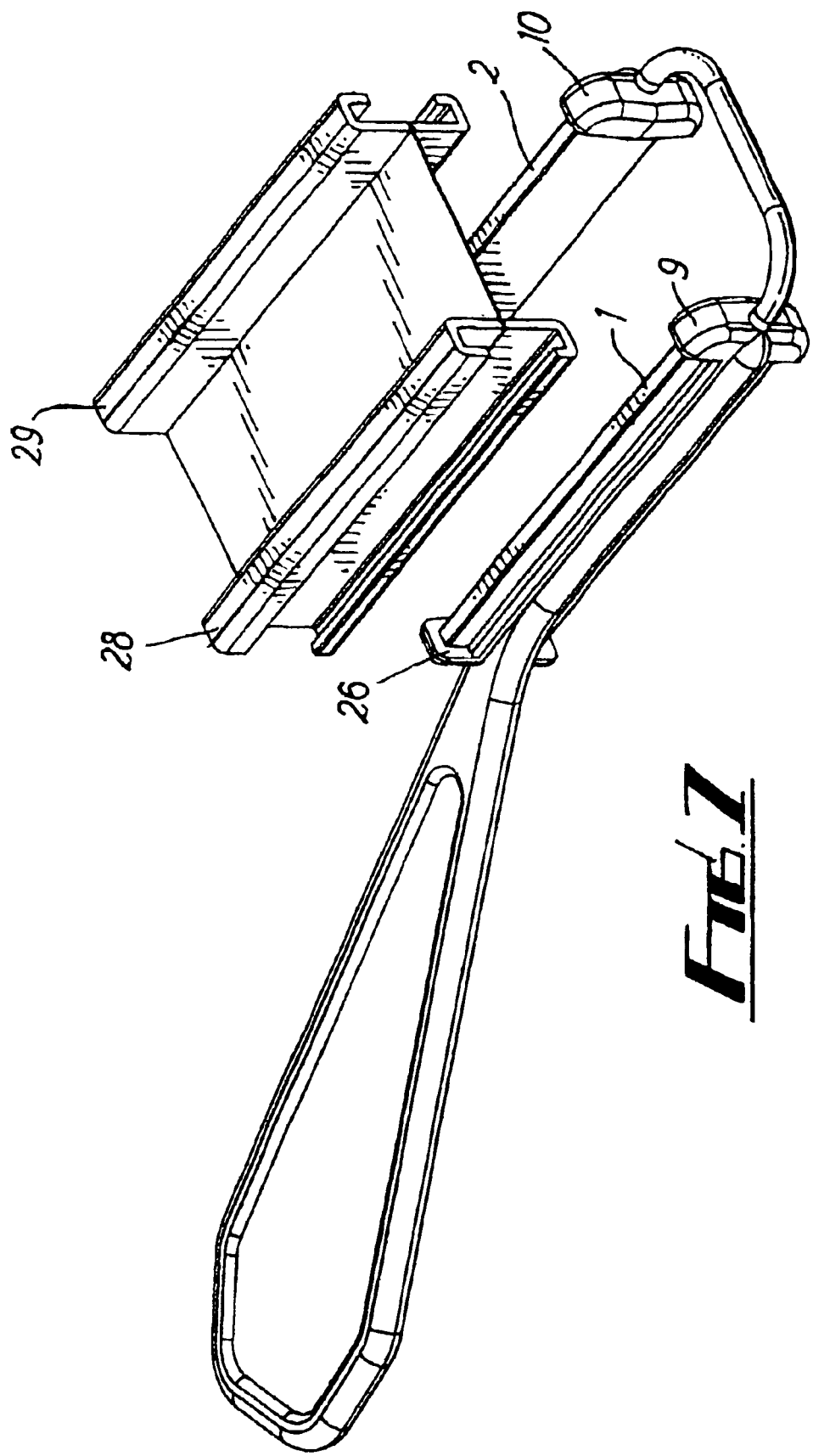
Figure 8:
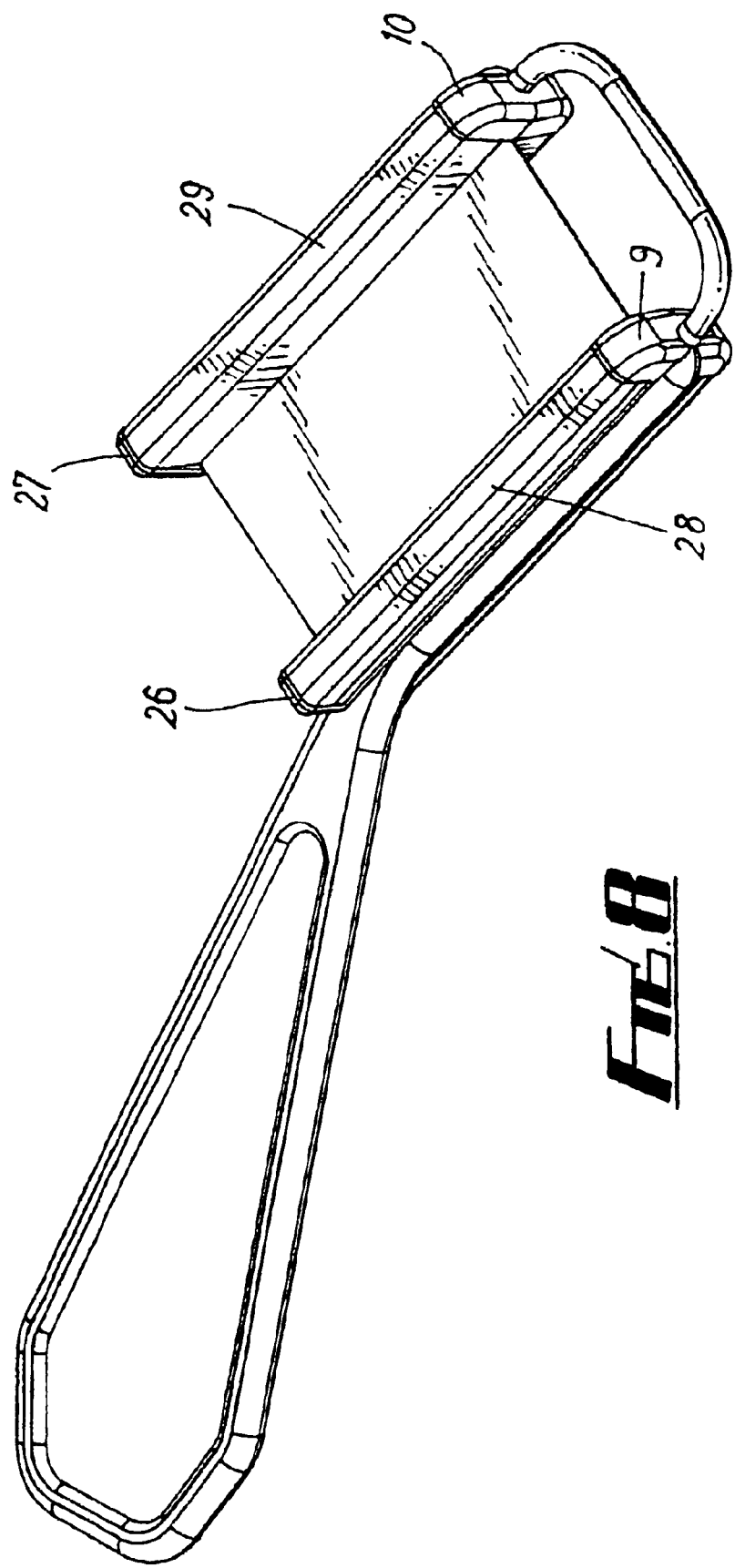

FIG. 5 a perspective view from the opposite side to that of FIG. 4, with the bite tray insert shown detached;

FIG. 6 is a perspective view of the arrangement of FIG. 4 with the bite tray insert attached;

FIG. 7 is a perspective view of a fourth embodiment of the dental apparatus of the invention with the bite tray insert shown detached; and FIG. 8 is a perspective view of the arrangement of FIG. 7 with the bite tray insert attached.

Figure 1:
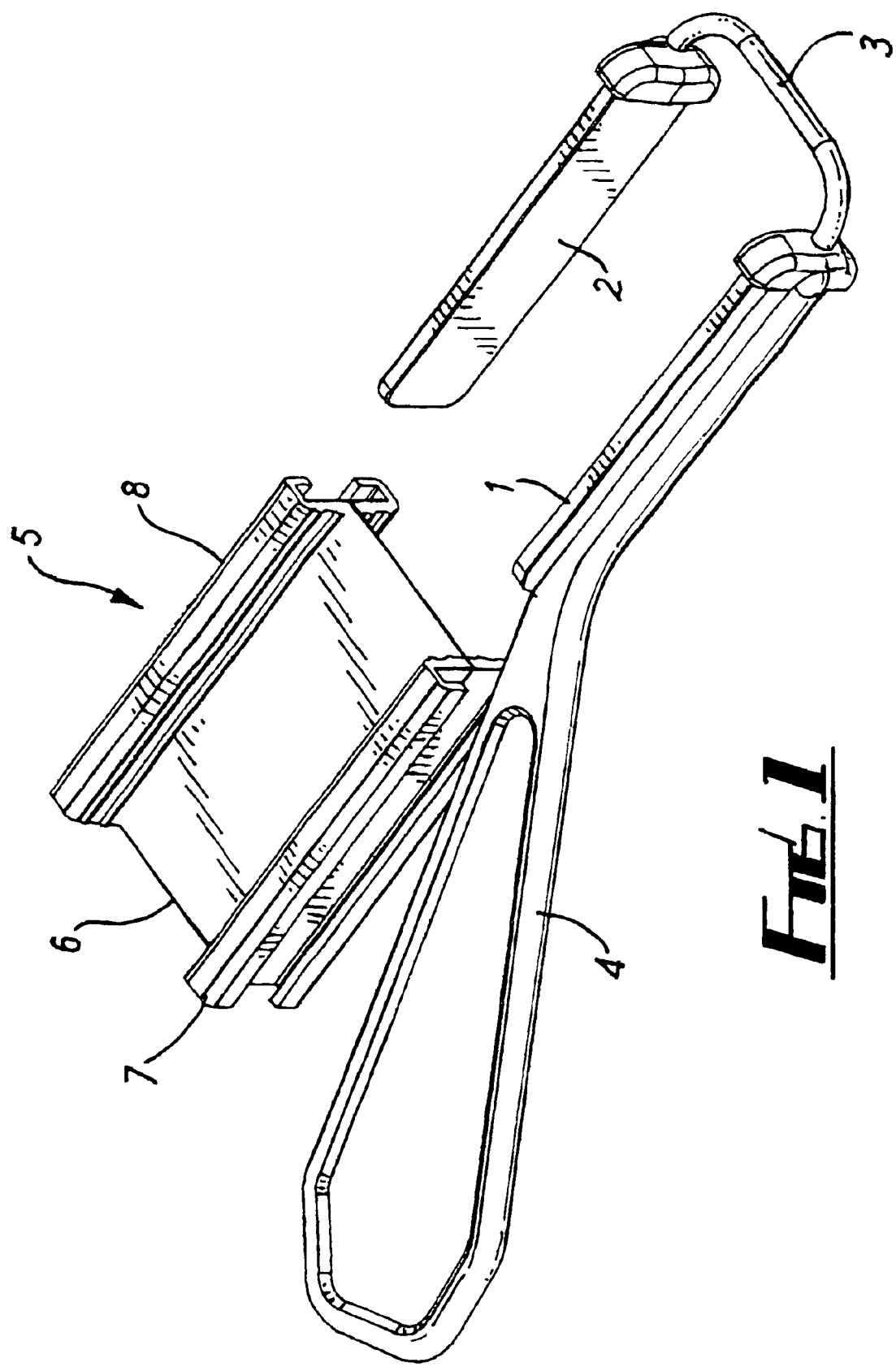
FIG. 1 is a perspective view of a first embodiment of the dental apparatus of the invention with the bite tray insert detached.

Referring to the drawings a first embodiment of the dental apparatus is illustrated in FIG. 1. The apparatus comprises a pair of elongate bite tray insert supports 1 and 2 which are substantially parallel and laterally spaced apart. At one end the bite tray insert supports 1 and 2 are connected together at corresponding adjacent ends of the supports 1, 2 by an arcuate frame 3 which maintains the orientation of the bite tray insert supports 1 and 2 in relation to each other. At the opposite end the supports are not connected thereby defining a free opening between the adjacent ends of the supports. The frame 3 is made from a rigid material such as stainless steel or a suitable plastics material. The bite tray insert supports 1 and 2 are made from a similar rigid material to that of the frame 3.

The bite tray insert supports 1 and 2 consist of elongate flat rails which have flat, confronting inner faces.

A handle 4 is provided attached to the outer face of one support 1. In addition, the handle 4 is located at the end of the support 1 which is remote from the end which is in connection with the frame 3 and extends outwardly at an angle away from the support 1 and the frame 3.

The apparatus comprises further a bite tray insert 5 which consists of a body of material 6 which transversely extends between, and is secured to, the rear sides of a pair of grooved members 7 and 8. The body of material 6 is a gauze or a perforate material made from plastics materials but could equally be made from a woven textile material. The width of the body of material 6 is substantially equal to the distance between the inner faces of the pair of bite tray insert supports 1 and 2, and has a length which is less than the length of the bite tray insert supports 1 and 2.

The grooved members 7 and 8 have inner dimensions which are sufficient to allow the bite tray insert supports 1 and 2 to be received therein whilst providing a releasably secure engagement there between. In order to allow the bite tray insert supports 1 and 2 to be received in the grooved members 7 and 8, said grooved members 7 and 8 are open at each end thus allowing the supports 1 and 2 to protrude through and out of the ends of the grooved members 7 and 8.

Figure 2:
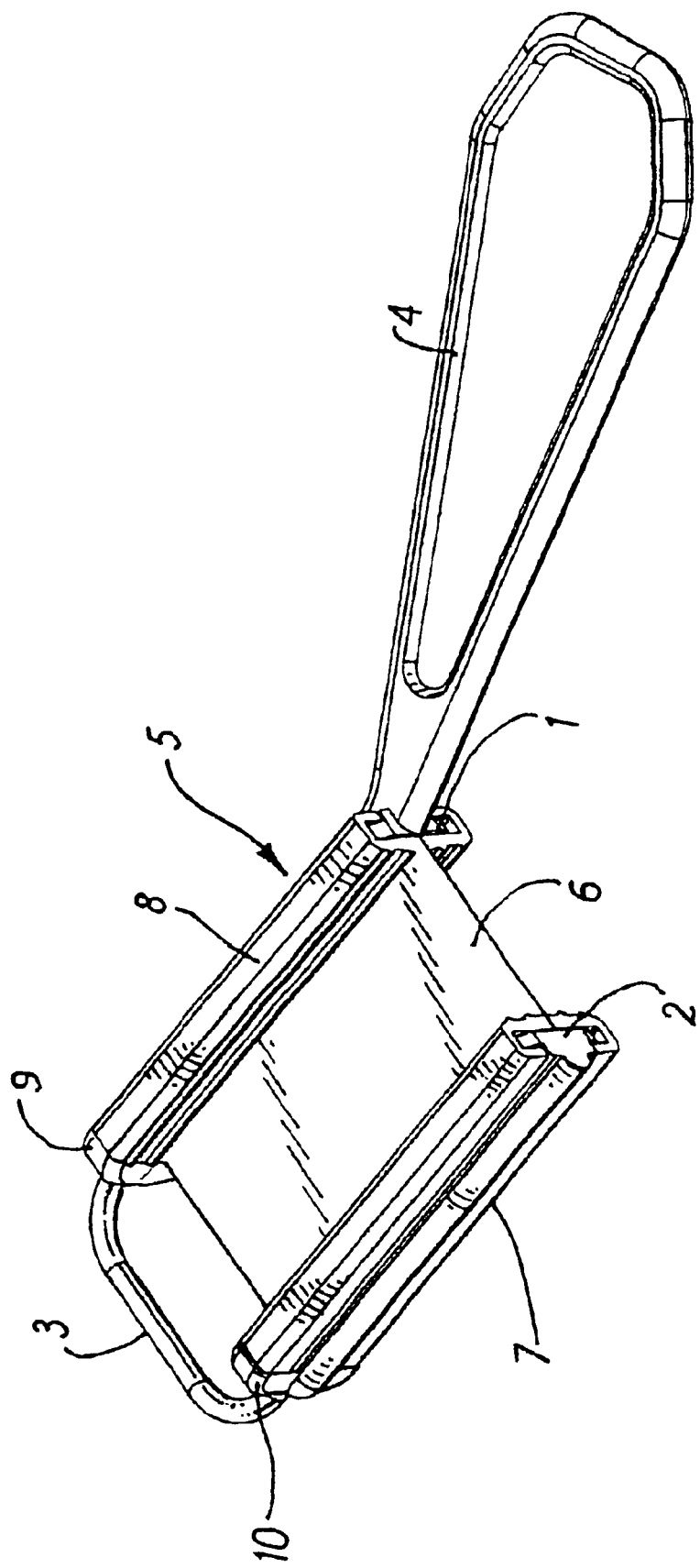
FIG. 2 is a perspective view, from an opposite side to that of FIG. 1, of the apparatus assembled with the bite tray insert.

An assembled first embodiment of the dental instrument is shown in FIG. 2 which illustrates how the bite tray insert 5 is connected to the bite tray insert supports 1 and 2. The bite tray insert supports 1 and 2 are each provided with an outwardly extending flange 9 and 10 which act as an abutment means in order to suitably position the bite tray insert 5 when in connection with the bite tray insert supports 1 and 2.

Each support 1,2 has along its outer face a central outwardly projecting longitudinal ridge which fits between rims bounding the openings along the grooved members 7,8.

Figure 3:
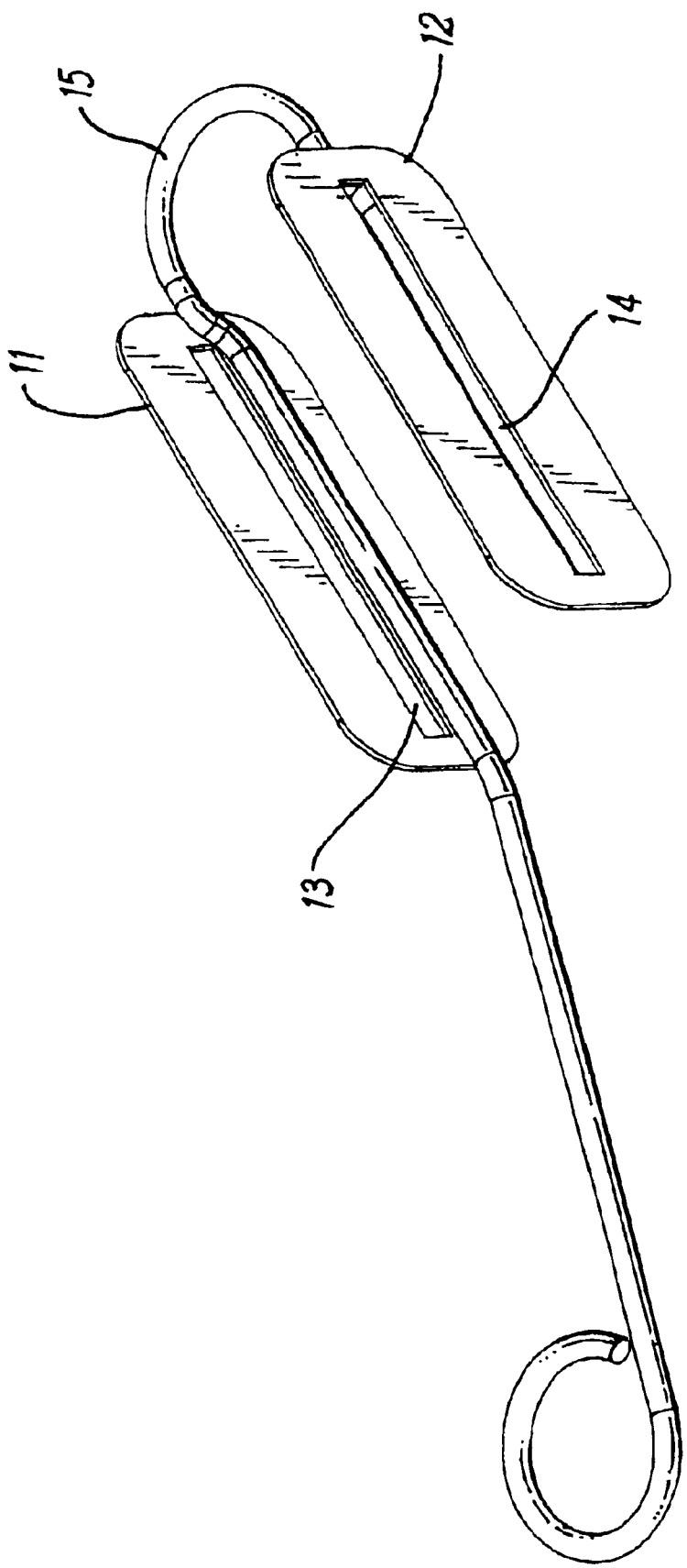
FIG. 3 is a perspective view of a second embodiment of the dental apparatus of the invention.

A second embodiment of the dental apparatus is shown in FIG. 3. This embodiment comprises a pair of elongate plates 11 and 12 each having an elongate rectangular aperture 13 and 14 therethrough. The pair of plates 11 and 12 are fixed in parallel and spaced apart orientation to each other by a connected frame 15. The frame 15 has an arcuate section which extends into two straight parallel and spaced apart sections which are connected to the inner sides of the plates 11 and 12 which face each other without obscuring the apertures 13 and 14. One of said straight sections of the frame 15 extends past the plate 11 and at an angle away therefrom to form a handle provided with a loop at the end thereof for ease of manipulation.

In use the embodiment shown in FIG. 3 uses a conventional bite tray insert (not shown) which comprises a length of gauze/perforate supporting material which is substantially the same width as the distance between the pair of plates 11 and 12, this material extending between, and being secured to, a pair of transverse upstanding elongate flanges having a width substantially the same as the width of the plates. To releasably engage the bite tray insert to the plates 11 and 12 one flange is deflected so as to lie generally in the plane of the supporting material and is slotted through one of the apertures 13 or 14. Once through, the first flange return to its upstanding condition and the second flange is used to pull the first flange flush against the plate 11 or 12. Thereafter, the second flange is deflected and slotted through the other aperture 13 or 14, and once through, the gauze material's inherent resilience will pull the second flange flush against the outer side of the plate 11 or 12.

Alternatively, in order to manipulate the second flange through the other aperture 13 or 14 the two plates may be squeezed toward each other and, once through, the flange will be drawn flush against the plate 11 or 12 due to the resilience of the frame 15.

A third embodiment of the dental apparatus is shown in FIG. 4, FIG. 5 and FIG. 6. The arrangement of the elongate bite tray insert supports 16 and 17 is clearly illustrated in FIG. 4. The bite tray insert supports 16 and 17 is parallel and spaced apart from each other and each have an elongate slot 18 and 19 therein. On the rear side of each support 16 and 17, the rear side being the side opposite to the sides facing each other, are two abutment means positioned substantially at each end of each support 16 and 17.

The bite tray insert supports 16 and 17 are maintained in their specific orientation to each other by connection to a frame 20. The frame is connected to the ends of the bite tray insert supports 16 and 17 which are remote from the slot openings 18 and 19. A handle 21 is attached to the bite tray insert support 1 B in order to facilitate the manoeuverability of the instrument but which does not obstruct the opening of the slot 18.

The bite tray insert 22 which is to be used in conjunction with the third embodiment of the invention is shown in FIG. 5. The bite tray insert comprises a body of gauze/perforate material 23 which is substantially the same width as the distance between the pair of bite tray insert supports 16 and 17. This body of material 23 extends between, and is secured to, a pair of elongate flanges 24 and 25.

FIG. 6 illustrates the assembled third embodiment. This drawing illustrates that the elongate flanges 24 and 25 are shorter in length than the distance between the abutment means. It can be envisaged that in use the material 23 of the bite tray insert 22 is inserted into slots 18 and 19 thus moving the elongate flanges 24 and 25 over and adjacent to the rear side of the bite tray insert supports. The material 23 of the bite tray insert is inserted far enough into the slots 18 and 19 until the elongate flanges 24 and 25 are positioned in between the abutment means of the rear side of the bite tray insert supports.

With the embodiment described above, interengagement between longitudinal members on opposite edges of the bite tray insert supporting material with longitudinal supports of the dental apparatus is facilitated whereby the bite tray insert can be conveniently mounted on and removed from the supports. It provides goods support for dental impression material when in use and permits easy detachment for disposal and replacement.

A fourth embodiment of the dental apparatus is shown in FIG. 6. This embodiment is identical to the first embodiment except that each of the bite tray insert supports 1 and 2 have an additional outwardly extending flange 26 and 27 which extend from the end of the supports 1 and 2 remote from the flanges 9 and 10. The additional outwardly extending flanges 26 and 27 act as a second abutment means.

The bite tray insert is identical to the insert shown with the first embodiment except that the grooved members 28 and 29 are made from a resilient or rigid material. The nature of the material used to make the grooved members 28 and 29 allows the members 28 and 29 to be vertically pushed over the supports between the pair of flanges on each support 1 and 2 and form a snap-fit engagement therewith.

The fourth embodiment of the dental apparatus connected with the bite tray via a snap-fit engagement is shown in FIG. 7.

It is to be understood that the above described embodiment is by way of illustration only. Many modifications and variations are possible.

What is claimed is:

1. Dental apparatus comprising:
a bite tray insert having a body of supporting material with opposed edges having longitudinal members thereat extending transversely to the supporting material, and
a pair of spaced apart bite tray insert supports comprising rails which at one end are connected together and opposite thereto have adjacent ends defining therebetween a free opening, said supports being adapted for releasable engagement with the longitudinal members of the bite tray insert, whereby the supporting material is suspended between innermost faces of the supports,
wherein the longitudinal members each comprise an outward-facing grooved member and the longitudinal members are engageable with the rails by sliding longitudinally onto the rails, whereby the longitudinal members extend over the innermost face of the rails to protect such innermost face from impression material on the supporting material.

2. Dental apparatus according to claim 1 wherein the supports are interconnected at one end by means of a frame structure.

3. Dental apparatus according to claim 2 wherein a handle is provided connected to one of the supports.

4. Dental apparatus according to claim 3 wherein the handle extends outwardly from one of the supports at an acute angle away from the support at the opposite end to the frame structure.

5. Dental apparatus according to claim 1 wherein the supports are provided with abutments to limit movement of the longitudinal members along the supports.

6. Dental apparatus according to claim 1 wherein the width of the body of supporting material of the bite tray insert is substantially the same width as the distance between the inner faces of the bite tray insert supports.

7. Dental apparatus according to claim 1 wherein the longitudinal members are adapted for snap-fit connection transversely over the bite tray insert supports.

8. Dental apparatus according to claim 1 wherein the body of supporting material transversely extends between and is secured to rear sides of the grooved members.

9. Dental apparatus according to claim 1 wherein each rail has along its outer face a central outwardly projecting longitudinal ridge which fits between rims bounding the openings along the grooved members.

10. Dental apparatus according to claim 1 wherein rims bounding openings along the grooved members extend outwardly from the top and the bottom of the grooved members.

* * * * *